United States Patent [19]
Philipp et al.

[11] 3,950,343
[45] Apr. 13, 1976

[54] PYRROLOISOQUINOLINE DERIVATIVES

[75] Inventors: Adolf H. Philipp; Christopher A. Demerson, both of Montreal; Leslie G. Humber, Dollard-des-Ormeaux, all of Canada

[73] Assignee: Ayerst, McKenna and Harrison Ltd., Montreal, Canada

[22] Filed: Nov. 6, 1973

[21] Appl. No.: 413,417

[52] U.S. Cl. 260/288 CF; 260/283 SY; 260/326.13 R; 260/326.14 R; 424/258
[51] Int. Cl.²........................................ C07D 471/06
[58] Field of Search................... 260/288 R, 288 CF

[56] References Cited
UNITED STATES PATENTS

| | | | |
|---|---|---|---|
| 3,272,804 | 9/1966 | Archer et al. | 260/288 R |
| 3,330,835 | 9/1967 | Hester | 260/287 R |
| 3,833,591 | 9/1974 | McManus | 260/288 R |

OTHER PUBLICATIONS

Horning et al., Can. Jour. of Chem., Vol. 49, pp. 2797–2802, 1971.

*Primary Examiner*—Alton D. Rollins
*Assistant Examiner*—Mary Vaughn
*Attorney, Agent, or Firm*—John P. Floyd

[57] ABSTRACT

1,3,4,5-Tetrahydropyrrolo[4,3,2-de]isoquinoline and its N-alkyl derivatives are disclosed. The compounds are antidepressant and antihypertensive agents. Methods for their preparation and use are disclosed.

17 Claims, No Drawings

PYRROLOISOQUINOLINE DERIVATIVES

BACKGROUND OF THE INVENTION a. Field of Invention

This invention relates to pyrroloisoquinoline derivatives, to intermediates used in their preparation and to methods for preparing and using these compounds.

More specifically, this invention relates to pyrrolo[4,3,2-de]isoquinolines possessing central nervous system and circulatory system activities. For example, the compounds of this invention show antidepressant and antihypertensive properties in mammals at dose levels which do not elicit undesirable side effects. This combination of attributes render the pyrroloisoquinoline derivatives of the invention useful and desirable as therapeutic agents.

b. Prior Art

Prior interest in the field of pyrroloisoquinolines seems to be practically nonexistent. The only reference to this unusual ring system appears to be a recent chemical paper, D. E. Horning, et al., Can. J. Chem., 49, 2797 (1971), in which the main object of the paper was the preparation of particular 2-substituted 4-indolecarboxylic acids, a 1,3,4,5-tetrahydropyrrolo[4,3,2-de]-isoquinolin-5-one intermediate being isolated in the process.

On the other hand some interest has been shown for the related field of pyrroloquinolines and 1H-azepino[4,3,2-cd]indoles. For example, see J. B. Hester, J. Org. Chem. 29, 1158 (1964) and 32, 4095 (1967); see also U.S. Pat. No. 3,330,835, issued July 11, 1967 and U.S. Pat. No. 3,314,942, issued Apr. 18, 1967. However, the compounds of the present invention are distinguished from these prior art compounds by their different ring structure and pharmacologic properties.

SUMMARY OF THE INVENTION

The pyrroloisoquinolines of this invention are represented by formula 1

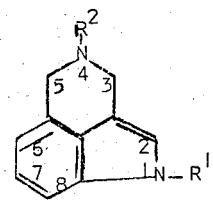

in which $R^1$ and $R^2$ each are hydrogen, lower alkyl or di(lower)alkylamino(lower)alkyl in which the alkylene portion thereof contains from two to six carbon atoms.

DETAILED DESCRIPTION OF THE INVENTION

The term "lower alkyl" as used herein contemplates straight chain alkyl radicals containing from one to six carbon atoms and branched chain alkyl radicals containing from three to four carbon atoms and includes methyl, ethyl, propyl, isopropyl, butyl, isobutyl, pentyl and the like.

The term "lower alkanoyl" as used herein contemplates both straight and branched chain alkanoyl radicals containing from two to six carbon atoms and includes acetyl, propionyl, hexanoyl and the like.

The term "lower alkanoic acid" as used herein contemplates both straight and branched chain acids containing from two to six carbon atoms and includes acetic acid, propionic acid, 3,3-dimethylbutyric acid and the like.

The term "halogen" as used herein contemplates chlorine, bromine and iodine.

The compounds of formula 1 are capable of forming acid addition salts with pharmaceutically acceptable acids. Such acid addition salts are included within the scope of this invention.

The acid addition salts are prepared by reacting the corresponding base form of the compound of formula 1 with at least one equivalent, or preferably with an excess of the appropriate acid in an organic solvent, for example, ether or an ethanol-ether mixture. These salts, when administered to mammals, possess the same pharmacologic activities as the corresponding bases. For many purposes it is preferable to administer the salts rather than the base compounds. Among the acid addition salts suitable for this purpose are salts such as the sulfate, phosphate, lactate, tartrate, maleate, citrate, hydrobromide and hydrochloride. Both the base compounds and the salts have the distinct advantage of possessing a relatively low order of toxicity.

The antidepressant activity of the pyrroloisoquinolines of formula 1 and their acid addition salts with pharmaceutically acceptable salts is demonstrated in standard pharmacologic tests such as, for example, the tests described by F. Hafliger and V. Burckhart in "Psychopharmacological Agents", M. Gordon, Ed., Academic Press, New York and London, 1964, pp. 75–83.

More specifically, as noted in the latter reference the antidepressant properties of a compound may be demonstrated by its capacity to antagonize the depressant effects of reserpine. Furthermore, it is well documented that reserpine in animals produces a model depression which can be used for detecting antidepressant properties. Accordingly, the compounds of the present invention antagonize reserpine effects in mice at doses ranging from about 1 to 100 mg/kg. Several of the preferred compounds, for instance, 1,3,4,5-tetrahydro-1-methylpyrrolo[4,3,2-de]isoquinoline hydrochloride (Example 6),
1,3,4,5-tetrahydro -1,4-dimethylpyrrolo[4,3,2-de]isoquinoline hydrochloride (Example 7),
1-ethyl-1,3,4,5-tetrahydropyrrolo[4,3,2-de]isoquinoline hydrochloride (Example 6), and
4-ethyl-1,3,4,5-tetrahydro-1-methylpyrrolo[4,3,2-de]isoquinoline hydrochloride (Example 8), antagonize the effects or reserpine in mice at dose ranges from about 1 to 15 mg/kg.

When the pyrroloisoquinolines of this invention are used as antidepressants in warm-blooded mammals, e.g. rats and mice, they may be used alone or in combination with pharmacologically acceptable carriers, the proportion of which is determined by the solubility and chemical nature of the compound, chosen route of administration and standard biological practice. For example, they are administered orally in solid form containing such excipients as starch, milk sugar, certain types of clay and so forth. They may also be administered orally in the form of solutions or they may be injected parenterally. For parenteral administration they may be used in the form of a sterile solution containing other solutes, for example, enough saline or glucose to make the solution isotonic.

The dosage of the present therapeutic agents will vary with the form of administration and the particular compound chosen. Furthermore, it will vary with the particular host under treatment. Generally, treatment is initiated with small dosages substantially less than the optimum dose of the compound. Thereafter, the dosage is increased by small increments until the optimum effect under the circumstance is reached. In general, the compounds of this invention are most desirably administered at a concentration level that will generally afford effective results without causing any harmful or deleterious side effects and preferably at a level that is in a range of from about 0.1 mg to about 100 mg per kilo per day, although as aforementiond variations will occur. However, a dosage level that is in the range of from about 0.5 mg to about 50 mg per kilo per day is most desirably employed in order to achieve effective results.

The antihypertensive effect of the pyrroloisoquinoline of formula 1 and their acid addition salts is demonstrated also in standard tests, for example, in tests conducted in the spontaneously hypertensive rat such as described by R. Tabei, et al., Clin. Pharmacol. Therap., 11, 269 (1970).

When the pyrroloisoquinolines of this invention are employed as antihypertensive agents they are formulated and administered in the same manner as described above for their use as antidepressant agents.

PROCESS

A preferred process for the preparation of the pyrroloisoquinolines of formula 1 is illustrated in the following flow diagram.

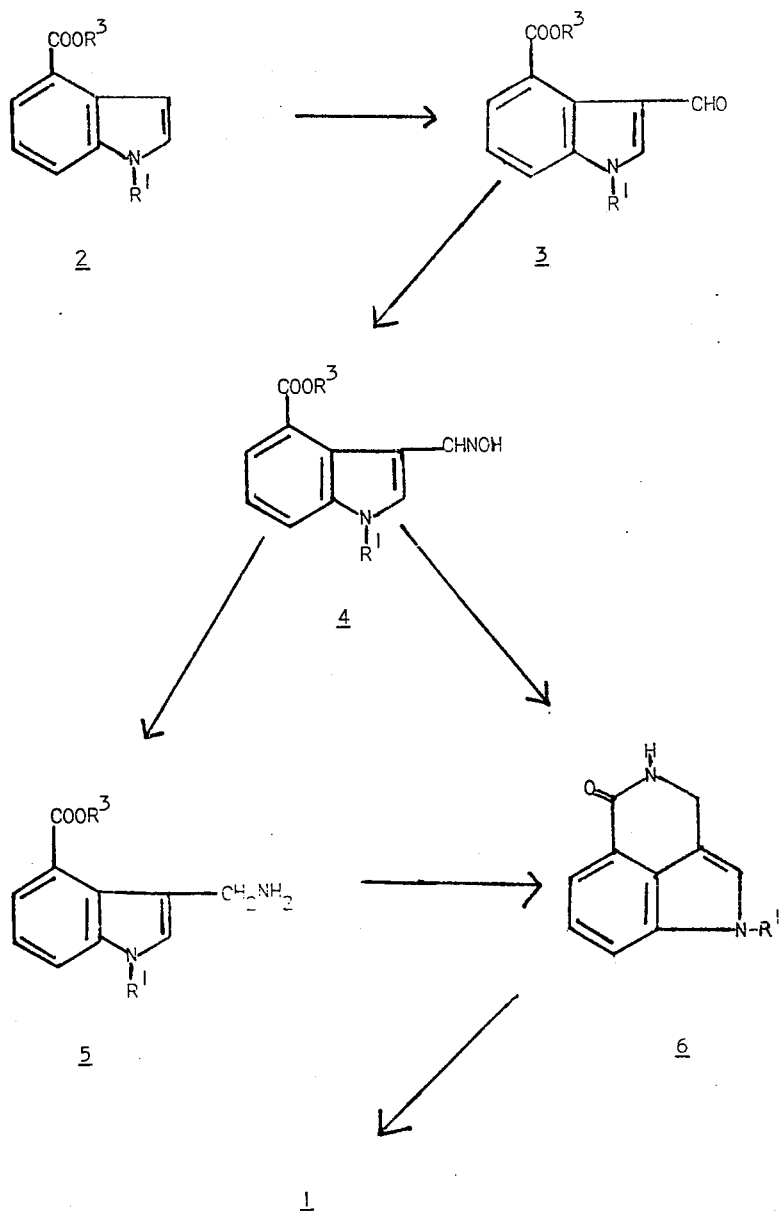

The starting material for the preferred process of this invention is a compound of formula 2 in which $R^1$ is hydrogen or lower alkyl and $R^3$ is lower alkyl. The compound of formula 2 in which $R^1$ is hydrogen and $R^3$ is methyl, 4-indolecarboxylic acid methyl ester, has been described by F. C. Uhle, J. Amer. Chem. Soc., 71, 761 (1949). The compounds of formula 2 in which $R^1$ is lower alkyl are prepared from the corresponding lower alkyl esters by a standard N-alkylation reaction using substantially one equivalent of an alkylating agent in the presence of a proton acceptor in an inert solvent. Convenient conditions for the preparation of these compounds of formula 2 ($R^1$ = lower alkyl) include the use of the appropriate alkyl halide, for example methyl iodide, ethyl bromide, propyl chloride and the like, in the presence of the proton acceptor, sodium hydride, and benzene as the solvent.

Other corresponding lower alkyl esters, for example those in which $R^3$ represents ethyl, propyl, isobutyl and the like, are prepared from 4-indolecarboxylic acid, described by Uhle, cited above, by conventional esterification processes; preferably esterification with an appropriate lower alkanol in the presence of an acid catalyst.

With reference to the process for preparing the pyrroloisoquinolines of formula 1, the starting material of formula 2 is subjected to formylation by means of an alkyl aryl or dialkyl formamide, for example, N-methylformanilide or dimethylformamide, in the presence of phosphorus oxychloride, phosphorous oxybromide, phosgene or thionylchloride, according to conditions to the Vilsmeier reaction. Preferred reaction conditions fo this reaction include temperatures ranging from 20°–65°C, a reaction time of from one to four hours and the use of ethylene dichloride or benzene as the solvent. In this manner, the corresponding compound of formula 3 in which $R^1$ and $R^3$ are as defined hereinbefore is obtained.

The latter compound is converted to its corresponding oxime of formula 4 by treatment with hydroxylamine, preferably hydroxylamine hydrochloride in the presence of sodium acetate.

Thereafter this oxime is transformed to the tricyclic amide 6 in which $R^1$ is as defined hereinbefore by either a one or two step process. In the case of the one step process the oxime is reduced catalytically under alkaline conditions. The reduction is accomplished by using gaseous hydrogen and a hydrogenation catalyst in the presence of an alkaline agent. Suitable reducing conditions include the use of noble metal catalyst, for example, palladium, platinum, palladium oxide or platinum oxide, an inert carrier such as charcoal and sodium or potassium acetate as the alkaline agent. Alternatively one of the preceding catalyst are suspended on the akaline agent, for example, alumina. Again alternatively, the use of Raney nickel alone serves simultaneously as the hydrogen source, catalyst and the basic agent. The reaction is performed in an inert organic solvent, for example, methanol, ethanol, tetrahydrofuran and the like, methanol being preferred, at atmospheric pressure or up to one atmosphere of pressure. The temperature of the reaction is not critical and may vary from room temperature to about 100°C, room temperature being preferred. The duration of the reaction will vary depending on the catalyst, temperature and hydrogen pressure employed. Normally the reaction is allowed to proceed until the required amount (two molecular equivalents) is absorbed. In this manner the tricyclic amide 6 is obtained directly.

Alternatively, a two-step process is conveniently employed for the transformation of oxime to the tricyclic amide. In this case the oxime is reduced catalytically in the same manner as described above except under neutral or acidic conditions whereby the corresponding aminoester of formula 5 is obtained. In other words the catalytic reduction is carried out according to the above described conditions but the alkaline agent is omitted or replaced with an acid agent.

When an acid is employed in the present reduction medium, the aminoester is otained as the corresponding acid addition salt of said acid. Preferred conditions for this reduction include the use of the above noble metal catalyst in the presence of at least one equivalent of hydrochloric acid or acetic acid. In act it has been found convenient to employ an excess of acetic acid so that the acetic acid serves simultaneously as the acidic agent and the solvent for the reduction.

In the second step of this two step process the aminoester is treated with a basic condensing agent to obtain the corresponding tricyclic amide of formula 6 in which $R^1$ is as defined hereinbefore. This second step proceeds smoothly and readily at room temperature when either the aminoester or one of its corresponding acid addition salts are brought into contact with at least one equivalent of the basic condensing agent. Preferred basic condensing agents for this step include alkali metal alkoxides, for example, sodium methoxide or potassium tert-butoxide, and the alkali metal hydroxides or carbonates, for example sodium hydroxide or potassium carbonate. The reaction is carried out most conveniently in an inert solvent, preferably the corresponding alkanol if an alkali metal alkoxide is being employed or a mixture of water and a lower alkanol, for instance methanol, if the alkali metal hydroxides or carbonates are being employed.

At this point, having obtained the tricyclic amide 6 in which $R^1$ is as defined hereinbefore by either of the above two methods the said amide is reduced chemically to give the corresponding pyrroloisoquinoline of formula 1 in which $R^1$ is as defined hereinbefore and $R^2$ is hydrogen.

This present reduction is accomplished by treatment of the amide 6 with diborane, an amine-diborane complex, or by treatment of the amide with a suitable metal-acid reducing system. Treatment with diborane has been found to be both efficient and convenient. When using diborane or an amine-diborane complex, for example, diborane complexes with ethylamine or tert-butyl amine, the reduction is conveniently performed by bringing the tricyclic amide into contact with two to five molecular equivalents of the reducing agent in an inert solvent, for example, tetrahydrofuran or ether, at temperatures of −10° to 80°C, or the boiling points of the reaction solvent. A reaction period of 30 minutes to 2 or 3 days is employed. With diborane the reaction is usually initiated at 0° to 10°C and then brought to the boiling point of the reaction solvent.

When a metal-acid system is employed for this latter reduction, the tricyclic amide is preferably dissolved in an inert solvent, preferably, ethanol or tetrahydrofuran, treated simultaneously and portionwise with the metal and acid at temperatures from 20° to 80° for a period of 2 to 20 hours. Suitable metal-acid combinations for this reduction include zinc-hydrochloric acid, zinc-acetic acid and tin-hydrochloric acid.

In the preceding manner, therefore, the pyrroloisoquilines of formula 1 in which $R^1$ is hydrogen or lower alkyl and $R^2$ is hydrogen, are obtained.

Alternatively the latter compounds of formula 1 in which $R^1$ is lower alkyl are prepared by first temporarily protecting the isoquinolinic nitrogen of the pyrroloisoquinoline compound of formula 1 in which $R^1$ and $R^2$ each are hydrogen. Such temporary protection is achieved readily by treating the latter compound with benzyl chloroformate in the presence of a base, for example, pyridine or triethylamine, to obtain the corresponding compound of formula 1 in which $R^1$ is hydrogen and $R^2$ is carbobenzyloxy, i.e. the carbobenzloxy group is preferentially formed on the isoquinolinic and not the indolic nitrogen.

The latter compound is subjected next to the N-alkylation with the appropriate alkyl halide in the same manner as described above for the N-alkylation of the compound of formula 2 to give the corresponding compound of formula 1 in which $R^1$ is lower alkyl. Subsequent removal of the protecting group, for example, hydrogenolysis with palladium catalyst to remove the carbobenzyloxy group, gives the desired pyrroloisoquinoline of formula 1 in which $R^1$ is lower alkyl and $R^2$ is hydrogen.

When it is desired to obtain the pyrroloisoquinolines of formula 1 in which $R^1$ is hydrogen or lower alkyl and $R^2$ is methyl, the appropriate pyrroloisoquiniline of formula 1 in which $R^1$ is hydrogen or lower alkyl and $R^2$ is hydrogen, described above, is treated with methyl or ethyl chloroformate in the presence of a proton acceptor, preferably triethylamine, to obtain the corresponding N-carboalkoxy derivative, for example the N-carbomethoxy or N-carboethoxy derivative, in which the N-carboalkoxy group has been formed preferentially on the isoquinolinic nitrogen, i.e., the corresponding compound of formula 1 in which $R^2$ is a N-carboalkoxy group. The latter compound is then reduced with lithium aluminum hydride to give the desired corresponding pyrroloisoquinoline of formula 1 ($R^2 = CH_3$).

When it is desired to obtain the pyrroloisoquinolines of formula 1 in which $R^1$ is hydrogen or lower alkyl and $R^2$ is lower alkyl other than methyl, the appropriate pyrroloisoquinoline with $R^2$ being hydrogen is converted into the corresponding acylated compound of formula 1 in which $R^2$ is lower alkanoyl by treatment under suitable acylating conditions. Suitable conditions for this conversion include the treatment of the pyrroloisoquinoline with $R^2$ being hydrogen with the appropriate lower akanoic acid anhydride or a lower alkanoic acid halide in the presence of a proton acceptor, preferably pyridine or triethylamine, for a period of two to four hours at room temperature. Note that under theseconditions the isoquinolinic nitrogen is preferentially acylated for the compound of formula 1 in which $R^1$ and $R^2$ each are hydrogen.

The latter acylated compound of formula 1 in which $R^1$ is hydrogen or lower alkyl transformed thereafter into the corresponding pyrroloisoquinoline of formula 1 in which $R^1$ is hydrogen or lower alkyl and $R^2$ is a lower alkyl other than methyl by treatment with lithium aluminum hydride.

When it is desired to prepare the compounds of formula 1 in which $R^1$ is di(lower)alkylamino(lower)alkyl, in which the alkylene portion thereof contains from two to six carbon atoms, the preferred mode entails N-alkylation of the lower alkyl ester, preferably the methyl ester, of 4-indolecarboxylic acid (2, $R^1$ = hydrogen and $R^3$ is lower alkyl) with the appropriate di(-lower)alkylamino(lower)alkyl halide, for example, 2-(diamethylamino)ethyl chloride or 3-(diethylamino)-propyl iodide, in same manner as described above for the previous N-alkylations. Thereafter the resulting compound of formula 2 ($R^1$ = di(lower)alkylamino(-lower)alkyl and $R^3$ = lower alkyl) is transformed by the aformentioned process of this invention to give the desired pyrroloisoquinolines.

Subsequent N-alkylation of the latter compounds again in the same manner with the appropriate lower alkyl halide or di(lower)alkylamino(lower)alkyl halide gives the corresponding pyrroloisoquinolines of formula 1 in which $R^1$ is di(lower)alkylamino(lower)alkyl and $R^2$ is lower alkyl or di(lower)alkylamino(lower)alkyl.

Alternatively, the pyrroloisoquinolines of formula 1 in which $R^1$ is di(lower)alkylamino(lower)alkyl and $R^2$ is lower alkyl are prepared directly by the above standard N-alkylation of the corresponding pyrroloisoquinoline of formula 1 in which $R^1$ is hydrogen and $R^2$ is lower alkyl, described previously, using the appropriate di(lower)alkylamino(lower)alkyl halide as the alkylating agent.

When it is desired to prepare the pyrroloisoquinolines of formula 1 in which R is hydrogen or lower alkyl and $R^2$ is di(lower)alkylamino(lower)alkyl with the proviso that the alkylene portion of the $R^2$ group contains from two to six carbon atoms, the preferred manner entails acylating the pyrroloisoquinoline of formula in which ¹ is hydrogen or lower alkyl and ² is hydrogen with an an appropriate acylating agent of the formula XCO—Alk—$X^1$ in which and $X^1$ are the same or different halogen as defined above and Alk is lower alkylene containing from one to five carbon atoms, in the presence of a proton acceptor, for example, triethylamine. In this manner the corresponding compound of formula 1 in which $R^2$ is CO—Alk—$X^1$ in which Alk and $X^1$ are as defined hereinbefore is obtained. Treatment of the latter compound with the appropriate secondary amine of formula $NHR^5R^6$ in which $R^5$ and $R^6$ each are lower alkyl, for example, dimethylamine or diethylamine, affords the corresponding compound of formula 1 in which $R^2$ is CO—Alk—$NR^5R^6$ in which Alk, $R^5$ and $R^6$ are as defined hereinbefore. In turn the latter compound is then reduced with lithium aluminum hydride to afford the desired pyrroloisoquinoline compound of formula 1 in which $R^1$ is hydrogen or lower alkyl and $R^2$ is di(lower)alkylamino(lower)alkyl in which the alkylene portion thereof contains from two to six carbon atoms.

Finally, it is the intention to cover all changes and modifications of the embodiment of this invention chosen herein for the purpose of this disclosure, which are within the scope and spirit of this invention. For example, the act of performing the N-alkylation reaction simultaneously on both nitrogens of a compound of formula 1 in which $R^1$ and $R^2$ each are hydrogen would not constitute a departure.

The following examples illustrate further this invention.

EXAMPLE 1

3-Formylindole-4-carboxylic acid methyl ester (3; $R^1$ = H and $R^3 = CH_3$)

To a stirred mixture of N-methylformanilide (15.6 g) and phosphorus oxychloride (17.7 g) is added ethylene dichloride (75 g ) followed by 4-indolecarboxylic acid methyl ester (17.5 g). The reaction mixture is stirred at room temperature for 1 1/2 hr., then at 45°–50°C for 30 minutes more. The mixture is now poured into a solution of 75 g of sodium acetate in 150 ml of ice-water.

More ethylene dichloride is added. The layers are separated and the organic phase is washed with water, dried ($Na_2SO_4$) and evaporated under reduced pressure. The residual brown oil is passed through a silica gel column using 3% methanol in chloroform. Concentration of the eluate affords a solid which on recrystallization from benzene affords the pure title compound, mp 135°C.

EXAMPLE 2

3- Formylindole-4-carboxylic acid methyl ester oxime (4; $R^1$ = H and $R^3$ = $CH_3$)

A mixture of 3-formyl -4-indolecarboxylic acid methyl ester (2.03 g), described in Example 1, 10 ml of a 5M aqueous solution of hydroxylamine hydrochloride, 10 of 5M aqueous sodium acetate and 20 ml. of methanol is stirred at 45°–55°C for 1 hr. The precipitate is collected and washed with cold water. Recrystallization from methanol-water gives the title compound, mp 178°-179°C.

EXAMPLE 3

3-(Aminomethyl)indole-4-carboxylic Acid Methyl Ester (5; $R^1$ ' H and $R^3$ = $CH_3$)

To 3-formylindole-4-carboxylic acid methyl ester oxime (1 g), described in Example 2, in 50 ml of methanol is added 5 ml of a saturated solution of HCl in methanol and 100 mg of 5% Pd/C. This mixture is stirred magnetically at room temperatue in a hydrogen atmosphere until hydrogen uptake ceases. The catalyst is collected on a filter and the filtrate concentrated to dryness under reduced pressure. The resulting powder is dissolved in ethanol and precipitated out with ether to afford the hydrochloric salt of the title compound, nmr($CDCl_3$) δ 4.05(3H), 4.28 (2H), 7.00–8.00 (4H).

The present intermediate can be used in the process of the invention as an acid addition salt, for example, the above hydrochloric salt. If desired, the corresponding free base, $\nu_{max}^{CHCl_3}$ 1736 $cm^{-1}$, is obtained by treating an anhydrous methanol solution of the salt with an equivalent of sodium methoxide, followed by filtration and concentration of the solution.

EXAMPLE 4

3,4- Dihydropyrrolo- [ 4,3,2 -de ]isoquinolin-5(1 H)-one ( 6; $R^1$ = H)

Preparation A:
A mixture of 3-formylindole -4-carboxylic acid methyl ester oxime (1.6 g), described in Example 2 and platinum oxide (120 mg) in 60 ml of acetic acid is stirred in a hydrogen atmosphere for 16 hr. Removal of the catalyst and concentration of the solution affords an oily residue [the acetic acid addition salt of 3-(aminomethyl)indole -4-carboxylic acid methyl ester]. The oil is suspended in water. The mixture is rendered alkaline with 10% NaOH. The solid is collected, triturated with 30% acetone in benzene and recrystallized from ethanol to afford the title compound, mp. 232°-234°C, $\nu_{max}^{CHCl_3}$ 1668 $cm^{-1}$.

Preparation B:
Sodium metal (19.2 g) is dissolved in absolute methanol (1 l.) with ice-water cooling. To the clear solution is added a solution of 3-(aminomethyl)indole-4-carboxylic acid methyl ester hydrochloride (102.7 g), described in Example 3, in absolute methanol (1 l.). The addition is done in portions within a few minutes. After stiring for 1.5 hr at room temperature the solution is concentrated to near dryness and ice cold water (250 ml) is added to the crystalline residue. The precipitate is collected, washed with cold water and dried to give the title compound, mp. 232°–234°C, identical to the product of Preparation A of this example.

EXAMPLE 5

1,3,4,5-Tetrahydropyrrolo[4,3,2-de]isoquinoline (1; $R^1$ and $R^2$ = H)

Preparation A:
3,4-Dihydropyrrolo[4,3,2-de]isoquinolin-5(1H)-one (40 g), described in Example 4, is added neat in portions during 15 minutes at −5° to 0°C to 700 ml of a 1M solution of diborane in tetrahydrofuran (THF). The reaction mixture is allowed to reach room temperature and kept there for 3 hr. The reaction mixture is then heated at reflux for 3.5 hr. After stirring overnight at room temperature 95% ethanol (360 ml) is added dropwise with cooling and stirring. Excess gaseous HCl is bubbled through the mixture while part of the solvent is removed by distillation. When the volume is reduced to ca. 200 ml, hot water (2 l.) is added to dissolve the crystalline precipitate. The clear acidic solution is stirred into a large excess of aqueous 20% NaOH. After stirring for one hr, the the precipitate is collected, thoroughly washed with water and dried to give the title compound, mp 240°–241°C, $\nu_{max}^{CHCl_3}$ 3300, 2900, 1607, 1595, 1530, 1510 $cm^{-1}$.

The corresponding hydrochloride salt of the title compound has mp 250°C (dec.), $\nu_{max}^{nujol}$ 3250, 1611, 1602, 1570, 1542 $cm^{-1}$, after recrystallization from methanol-ether.

Preparation B:
To a suspension of 3,4-dihydropyrrolo[4,3,2-de]-isoquinolin-5(1H) -one (1.0 g), described in Example 4, in ethanol is added mercurous chloride (25 mg), followed by simultaneous addition of Zn-dust (3.3 g) and conc. HCl ( 12 ml) during a period of 1.5 at reflux temperature. After 3 hr of reflux additional Zn-dust (3 g) and conc. HCl (2 ml) is added during one hour. The mixture is allowed to stand at room temperature overnight. The mixture is poured into aqueous NaOH and extracted with chloroform. The chloroform extract is treated with gaseous HCl to give the hydrochloride salt of the title compound.

EXAMPLE 6

1,3,4,5-Tetrahydro-1-methylpyrrolo[4,3,2-de]isoquinoline ( 1; $R^1$ = $CH_3$ and $R^2$ = H)

1,3,4,5-Tetrahydropyrrolo[4,3,2-de]isoquinoline (7.9 g), described in Example 5, is suspended in dry THF (60 ml). Triethylamine (23 ml) is added followed by dropwise addition of benzyl chloroformate (19 g) at 0°C. After stirring for 2 hr at room temperature the mixture is evaporated to near dryness. The residue is taken up in chloroform. The solution is washed with water, dried, treated with charcoal and taken to dryness. The residue is subjected to chromatography on silica gel. Elution with chloroform-methanol (19 : 1) gives an oil which on trituration with ether-hexane yields the carbamate, 1,3,4,5-tetrahydropyrrolo[4,3,2-de]isoquinoline-4-carboxylic acid benzyl ester, mp 142 20 -144°C.

The latter carbamate (9.2 g) is added at 0°C to a suspension of sodium hydride (5.4 g, 55% in mineral oil) in THF (100 ml) and the mixture kept at 40°C for 1 hr. Methyl iodide (3.2 ml) in THF (40 ml) is added with cooling during 15 minutes and the mixture is stirred at room temperature for 2.5 hr. Water is added dropwise to destroy the excess sodium hydride. The mixture is dried (MgSO$_4$) and taken to dryness. The residue is subjected to chromatography on silica gel. Elution with benzene-ethyl acetate (9 : 1) gives 1,3,4,5-tetrahydro-1-methylpyrrolo[4,3,2-de]isoquinoline-4-carboxylic acid benzyl ester.

The latter compound (9.5 g) dissolved in methanol (100 ml) is hydrogenolyzed at room temperature during 2 hr. using 5% palladium on charcoal as the catalyst. The catalyst is removed by filtration and the filtrate is concentrated to yield the title compound, nmr (CDCl$_3$) δ 3.70 (s, 3H), 4.12 (s, 4H), 6.6–7.15 (m,4H).

The corresponding hydrochloride of the title compound has mp >280°C (dec), $\nu_{max}^{nujol}$ 2800–1870, 1448 cm$^{-1}$.

By following the procedure of Example 6 but replacing methyl iodide with an equivalent amount of ethyl iodide, 1-ethyl-1,3,4,5-tetrahydropyrrolo[4,3,2-de]-isoquinoline (1, R$^1$ = C$_2$H$_5$ and R$^2$ = H), nmr (CDCl$_3$) δ 1.42 (t, J = 7, 3H), 4.15 (q, J = 7, 2H), 4.2 (m, 4H), 6.7–7.25 (m, 4H ), 6.7–7.25 (m, 4H), is obtained, via the intermediate 1,3,4,5-tetrahydro-1-ethylpyrrolo[4,3,2-de]isoquinoline-4-carboxylic acid benzyl ester, mp 112°–114°C. The corresponding hydrochloride salt of 1-ethyl-1,3,4,5-tetrahydropyrrolo[4,3,2-de]isoquinoline has mp 275°–276°C.

By following the procedure of Example 6 but replacing methyl iodide with an equivalent amount of propyl chloride, 1,3,4,5-tetrahydro-1-propylpyrrolo[4,3,2-de]isoquinoline is obtained.

EXAMPLE 7

1,3,4,5-Tetrahydro-4-methylpyrrolo[4,3,2-de]isoquinoline (1; R$^1$ = H and R$^2$ = CH$_3$)

To a suspension of 1,3,4,5-tetrahydropyrrolo[4,3,2-de]-isoquinoline (5 g), described in Example 5, in dry THF (65 ml) is added triethylamine (13.2 ml) followed by dropwise addition at 0°C of ethyl chloroformate (5.8 ml) in dry THF (65 ml). The reaction mixture is stirred at room temperature for 2 hr and then diluted with chloroform. The organic layer is separated, washed with NaHCO$_3$ and water, and then taken to dryness. The residue is subjected to chromatography on silica gel. Elution with benzene-ethyl acetate (1 : 1) gives 1,3,4,5-tetrahydropyrrolo[4,3,2-de]isoquinoline-d4-carboxylic acid ethyl ester, $\nu_{max}^{CHCl_3}$ 3465, 3310, 1675 cm$^{-1}$, nmr (CDCl$_3$) δ (t, J ' 7.5, 3H), 4.22 (q, J = 7.5, 2H), 4.92 (s, 4H), 6.7–7.25 (m,3H), 8.3 (broad s, 1H).

A solution of the latter compound (230 mg) in THF (5 ml) is added dropwise to an ice-cold suspension of lithium aluminum hydride (152 mg) in dry THF (5ml). The reaction mixture is stirred at room temperature for 2 hr. The excess reagent is destroyed by dropwise addition of water, and the mixture dried (MgSO$_4$). The organic phase is taken to dryness and the residue crystallized from ether-hexane to give the title compound, mp 185°–186°C, nmr (CDCl$_3$) δ 2.5 (s, 3H), 3.75 (s, 4H), 7.0 (m, 4H), 11.7 (broad s, 1 H).

The corresponding hydrochloride salt of the title compound has mp 243°–244°C after recrystallization from methanol-ether.

By following the procedure of Example 7 but replacing 1,3,4,5-tetrahydropyrrolo[4,3,2-de]isoquinoline with an equivalent amount of 1,3,4,5-tetrahydro-1-methylpyrrolo[4,3,2-de]isoquinoline, 1,3,4,5-tetrahydro-1,4-dimethylpyrrolo[4,3,2-de]isoquinoline(1, R$^1$ and R$^2$ = CH$_3$), nmr (CDCl$_3$) δ 2.55 (s, 3H), 3.7 (s, 3H), 3.82 (s, 4H), 6.65–7.2 (m, 4H), is obtained, via the intermediate, 1,3,4,5-tetrahydro-1-methylpyrrolo[4,3,2-de]isoquinoline-4-carboxylic acid ethyl ester, mp 76°–78°C. The corresponding hydrochloride salt of 1,3,4,5-tetrahydro-1,4-dimethylpyrrolo[4,3,2-de]isoquinoline has mp 250°–251°C.

By following the procedure of Example 7 but replacing 1,3,4,5-tetrahydropyrrolo[4,3,2-de]isoquinoline with an equivalent amount of 1,3,4,5-tetrahydro-1-propylpyrrolo[4,3,2-de]isoquinoline, described in Example 6, 1,3,4,5-tetrahydro-4-methyl-1-propylpyrrolo[4,3,2-de]isoquinoline is obtained.

EXAMPLE 8

4-Ethyl-1,3,4,5-tetrahydropyrrolo[4,3,2-de]isoquinoline (1; R$^1$ = H and R$^2$ = C$_2$H$_5$)

A mixture of 1,3,4,5-tetrahydropyrrolo[4,3,2-de]isoquinoline hydrochoride (9.8 g), described in Example 5, in 30 ml of pyridine and 10 ml of acetic anhydride is heated at 50°C for 2 hr. The excess anhydride is destroyed by the addition of water. The mixture is poured into cold 5% HCl. The resulting precipitate is collected and recrstallized from ethanol to give 4-acetyl-1,3,4,5-tetrahydropyrrolo[4,3,2-de]isoquinoline, mp 205°–206°C.

The latter compound (400 mg) is suspended in dry THF (30 ml) and lithium aluminum hydride (300 mg) is added. The mixture is stirred at room temperature for 45 minutes. The excess reagent is destroyed by addition of water and the mixture dried (MgSO$_4$). The solvent is evaporated to yield a light yellow solid which on recrystallization from methanol-water (charcoal treatment) gives the title compound, mp 191°–194°C, $\nu_{max}^{nujol}$ 3100, 1616, 1542, 1502 cm$^{-1}$.

The corresponding hydrochloride salt of the title compound has mp 265°–266°C after recrystallization from methanol-ether.

By following the procedure of Example 8 but replacing acetic anhydride with an equivalent amount of propionic anhydride, 4-propyl-1,3,4,5-tetrahydropyrrolo[4,3,2-de]isoquinoline is obtained.

By following the procedure to Example 8 but replacing 1,3,4,5-tetrahydropyrrolo[4,3,2-de]isoquinoline hydrochloride with an equivalent amount of 1,3,4,5-tetrahydro-1-methylpyrrolo[4,3,2-de]isoquinoline hydrochloride, described in Example 6, 4-ethyl-1,3,4,5-tetrahydro-1-methylpyrrolo[4,3,2-de]isoquinoline (1; R$^1$ = CH$_3$ and R$^2$ = C$_2$H$_5$), nmr (DMSO-$d_6$) δ 1.4 (t, J = 7, 3H), 3.2 (q, J = 7, 2H), 6.9–7.5 (m, 3H), is obtained via the intermediate, 4-acetyl-1,3,4,5-tetrahydro-1-methylpyrrolo[4,3,2-de]-isoquinoline, mp 125°–126°C. The corresponding hydrochloride salt of 4-methyl-1,3,4,5-tetrahydro-1-methylpyrrolo[4,3,2-de]isoquinoline has mp 249°–250°C.

EXAMPLE 9

1-[3(Dimethylamino)propyl]-1,3,4,5-tetrahydro-4-methylpyrrolo[4,3,2-de]isoquinoline (1; R$^1$ = (CH$_2$)$_3$N—(CH$_3$)$_2$ and R$^2$ = CH$_3$)

1,3,4,5-Tetrahydro-4-methylpyrrolo[4,3,2-de]isoquinoline (5.9 g), described in Example 7, in dimethylformamide (DMF, 100 ml) is combined at 0°C with a suspension of sodium hydride (15 g) in DMF (100 ml) and the mixture warmed at 40°C for 1.5 hr. 3-(Dimethylamino)propyl chloride (19 g) is added to the mixture with cooling. The reaction mixture is heated at 40°C for 1.5 hr. The mixture is poured on crushed ice, rendered acidic with HCl and washed with benzene. The aqueous phase is rendered alkaline with NaOH and extracted with benzene-chloroform. The extract is dried and taken to dryness. The residue is taken up in chloroform and treated with charcoal. The solution is evaporated to give the title compound, nmr (DMSO-$d_6$) δ 2.76 ($s$,6H), 2.9 ($s$,3H), 4.5 ($s$,4H).

The corresponding dihydrobromide salt of the title compound has mp 255°–258°C.

By following the procedure of Example 9 but replacing 3-(dimethylamino)propyl chloride with an equivalent amount of 2-(dimethylamino)ethyl iodide or 4-(diethylamino)butyl chloride, 1-[2-(dimethylamino)ethyl]-1,3,4,5-tetrahydro-4-methylpyrrolo[4,3,2-de]isoquinoline and 1-[4-(diethylamino)butyl]1,3,4,5-tetrahydro-4-methylpyrrolo[4,3,2-de]isoquinoline are obtained, respectively.

EXAMPLE 10

4-[3-(Dimethylamino)propyl]-1,3,4,5-tetrahydropyrrolo[4,3,2-de]isoquinoline [1; $R^1$ = H and $R^2$ = (CH$_2$)$_3$N(CH$_3$)$_2$]

To a suspension of 1,3,4,5-tetrahydropyrrolo[4,3,2-de]isoquinoline (3.24 g), described in Example 5, in chloroform (350 ml), triethylamine (6.0 ml) is added, followed by dropwise addition of 3-chloropropionyl chloride (4.2 ml). The mixture is stirred at room temperature for 2.5 hr. Aqueous sodium bicarbonate is added and the stirring is continued for 15 minutes. The layers are separated and the organic phase washed with water, dried and concentrated to give 4-(3-chloropropionyl)-1,3,4,5-tetrahydropyrrolo[4,3,2-de]isoquinoline, mp 158°–161°C after recrystallizaton from chloroform.

The latter compound (4.21 g) is dissolved with warming in ethanol (300 ml). At room temperature dimethylamine hydrochloride (5.51 g, 3 equiv. excess) and potassium hydroxide (5.15 g) are added and the mixture stirred overnight at room temperature. A precipitate is removed by filtration and the filtrate evaporated. The residue is taken up in chloroform. The solution is washed with potassium carbonate, water, then dried and taken to dryness to give a paste. Crystallization of the paste from chloroform-acetone-ether gives 4-[3-dimethylamino)propionyl]-1,3,4,5-tetrahydropyrrolo[4,3,2-de]isoquinoline, mp 106°–107°C.

To a solution of the latter compound (4.3 g) in dry THF (200 ml) a large excess of lithium aluminum hydride (3.1 g) is added. The mixture is stirred at room temperature for 0.5 hr. then water is added dropwise with cooling and stirring to destroy the excess reagent. The mixture is dried (MgSO$_4$). The solvent is evaporated to give the title compound, nmr (CDCl$_3$) δ 2.25 (6H), 1.5–3.0 ($m$, 6H), 3.96 (4H), 6.6–7.3 ($m$, 4H), 8.30 (1H).

The corresponding dihydrochloride salt of the title compound has mp 260°C (dec.).

By following the procedure of Example 10 but replacing 3-chloropropionyl chloride with an equivalent amount of chloroacetyl chloride or 4-bromobutyryl bromide, 4-[2-(dimethylamino)ethyl]-1,3,4,5-tetrahydropyrrolo[4,3,2-de]isoquinoline and 4-[4-(dimethylamino)butyl]-1,3,4,5-tetrahydropyrrolo[4,3,2-de]isoquinoline are obtained, respectively.

By following the procedure of Example 10 but replacing 1,3,4,5-tetrahydropyrrolo[4,3,2-de]isoquinoline with an equivalent amount of 1-ethyl-1,3,4,5-tetrahydropyrrolo[4,3,2-de]isoquinoline or 1,3,4,5-tetrahydro-1-propylpyrrolo[4,3,2-de]isoquinoline, described in Example 6, 4-[3(dimethylamino)propyl]-1-ethyl-1,3,4,5-tetrahydropyrrolo[4,3,2-de]isoquinoline and 4-[3-(dimethylamino)propyl]-1,3,4,5-tetrahydro-1-propylpyrrolo[4,3,2-de]isoquinoline are obtained, respectively.

We claim:
1. A compound of the formula

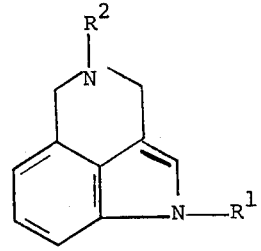

in which $R^1$ and $R^2$ each are hydrogen, lower alkyl having one to six carbons, when a straight chain alkyl, and from three to four carbons, when a branched chain alkyl or di(lower)alkylamino(lower)alkyl in which the alkylene portion thereof has from two to six carbons and the alkyl portion thereof has from one to six carbon atoms, when a straight chain alkyl, and from three to four carbon atoms, when a branched chain alkyl and the corresponding acid addition salts with pharmaceutically acceptable acids.
2. 1,3,4,5-Tetrahydro-1-methylpyrrolo[4,3,2-de]isoquinoline, as claimed in claim 1.
3. 1,3,4,5-Tetrahydro-1-methylpyrrolo[4,3,2-de]isoquinoline hydrochloride, as claimed in claim 1.
4. 1-Ethyl-1,3,4,5-tetrahydropyrrolo[4,3,2-de]isoquinoline, as claimed in claim 1.
5. 1-Ethyl-1,3,4,5-tetrahydropyrrolo[4,3,2-de]isoquinoline hydrochloride, as claimed in claim 1.
6. 1,3,4,5-Tetrahydro-4-methylpyrrolo[4,3,2-de]isoquinoline, as claimed in claim 1.
7. 1,3,4,5-Tetrahydro-4-methylpyrrolo[4,3,2-de]isoquinoline hydrochloride, as claimed in claim 1.
8. 1,3,4,5-Tetrahydro-1,4-dimethylpyrrolo[4,3,2-de]isoquinoline, as claimed in claim 1.
9. 1,3,4,5,-Tetrahydro-1,4-dimethylpyrrolo[4,3,2-de]isoquinoline hydrochloride, as claimed in claim 1.
10. 4-Ethyl-1,3,4,5-tetrahydropyrrolo[4,3,2-de]isoquinoline, as claimed in claim 1.
11. 4-Ethyl-1,3,4,5-tetrahydropyrrolo[4,3,2-de]isoquinoline hydrochloride, as claimed in claim 1.
12. 4-Ethyl-1,3,4,5-tetrahydro-1-methylpyrrolo[4,3,2-de]isoquinoline, as claimed in claim 1.
13. 4-Ethyl-1,3,4,5-tetrahydro-1-methylpyrrolo[4,3,2-de]isoquinoline hydrochloride, as claimed in claim 1.
14. 1-[3-(Dimethylamino)propyl]-1,3,4,5-tetrahydro-4-methylpyrrolo[4,3,2-de]isoquinoline, as claimed in claim 1.
15. 1-[3-(Dimethylamino)propyl]-1,3,4,5-tetrahydro-4-methylpyrrolo[4,3,2-de]isoquinoline dihydrobromide, as claimed in claim 1.

16. 4-[3-(Dimethylamino)propyl]-1,3,4,5-tetrahydropyrrolo[4,3,2-de]isoquinoline, as claimed in claim 1.

17. 4-[3-(Dimethylamino)propyl]-1,3,4,5-tetrahydropyrrolo[4,3,2-de]isoquinoline dihydrochloride, as claimed in claim 1.

* * * * *